United States Patent [19]

Chang et al.

[11] Patent Number: 5,690,934
[45] Date of Patent: Nov. 25, 1997

[54] PEPTIDES RELATING TO THE EXTRACELLULAR MEMBRANE-BOUND SEGMENT OF HUMAN ALPHA CHAIN

[75] Inventors: Tse Wen Chang; Nancy T. Chang, both of Houston, Tex.

[73] Assignee: Tanox Biosystems, Inc., Houston, Tex.

[21] Appl. No.: 619,790

[22] Filed: Mar. 20, 1996

Related U.S. Application Data

[63] Continuation-in-part of Ser. No. 249,558, May 26, 1994, and Ser. No. 180,145, Jan. 11, 1994, which is a continuation-in-part of Ser. No. 137,253, Oct. 14, 1993, which is a continuation-in-part of Ser. No. 90,527, Jul. 9, 1993, Pat. No. 5,342,924, which is a continuation-in-part of Ser. No. 973,321, Oct. 29, 1992, Pat. No. 5,254,671, which is a continuation-in-part of Ser. No. 515,604, Apr. 27, 1990, Pat. No. 5,274,075, which is a continuation-in-part of Ser. No. 468,766, Jan. 23, 1990, Pat. No. 5,260,416, which is a continuation-in-part of Ser. No. 369,625, Jun. 21, 1989, abandoned, which is a continuation-in-part of Ser. No. 272,243, Nov. 16, 1988, Pat. No. 5,091,313, which is a continuation-in-part of Ser. No. 229,178, Aug. 5, 1988, abandoned, which is a continuation-in-part of Ser. No. 226,421, Jul. 29, 1988, Pat. No. 5,422,258, which is a continuation-in-part of Ser. No. 140,036, Dec. 31, 1987, abandoned, said Ser. No. 249,558, is a continuation-in-part of Ser. No. 140,721, Oct. 22, 1993, Pat. No. 5,484,907, which is a continuation-in-part of Ser. No. 95,068, Jul. 20, 1993, Pat. No. 5,362,643, which is a continuation of Ser. No. 760,765, Sep. 16, 1991, abandoned, which is a continuation-in-part of Ser. No. 455,080, Dec. 22, 1989, Pat. No. 5,089,603, which is a continuation-in-part of Ser. No. 369,479, Jun. 21, 1989, Pat. No. 5,079,344.

[51] Int. Cl.$^6$ ................................................ A61K 39/395
[52] U.S. Cl. .................................... 424/178.1; 424/184.1; 424/130.1; 424/278.1; 436/513; 530/387.1; 530/387.3; 530/388.1; 530/389.1; 530/391.5
[58] Field of Search ........................ 424/178.1, 184.1, 424/130.1, 278.1, 804, 805; 436/513; 530/389.1, 391.5, 403, 810, 861, 862, 387.1, 387.3, 388.1

[56] References Cited

PUBLICATIONS

Sitia et al., "Membrane–Bound and Secreted IgA Contain Structurally Different α–Chains", J. Immunol. 128(2):712–716, Feb. 1982.
Cushley et al., Nature 298:577–79 (1982).
Burnett et al., EMBO J. 8:4041–47 (1989).
Robinson et al. PNAS 11:4909–13 (1980).
Osborne et al. 119:925–32 (1988).
Loghem et al. vol. 20 (1983).
Blattner et al. 307:417–22 (1984).

*Primary Examiner*—Laurie A. Scheiner
*Attorney, Agent, or Firm*—Eric P. Mirabel

[57] ABSTRACT

The invention relates to unique extracellular peptide segments present on B cell-bound but not secreted IgA. These extracellular peptide segments form, entirely or in part, antigenic epitopes unique to membrane-bound but not secreted IgA, and thereby provide a unique epitope on the IgA-bearing B cells to which membrane-bound IgA is attached. These peptide segments can be used as immunogens to generate antibodies which specifically target membrane-bound IgA and IgA-bearing B cells.

5 Claims, No Drawings

PEPTIDES RELATING TO THE EXTRACELLULAR MEMBRANE-BOUND SEGMENT OF HUMAN ALPHA CHAIN

RELATED APPLICATIONS

This application is a continuation-in-part of Ser. No. 08/249,558 pending), filed May 26, 1994, which is a continuation-in-part of Ser. No. 08/140,721, (U.S. Pat. No. 5,484,907), filed Oct. 22, 1993, which is a continuation-in-part of Ser. No. 08/095,068 (U.S. Pat. No. 5,362,643), filed Jul. 20, 1993, which is a continuation of Ser. No. 07/760,765 (abandoned), filed Sep. 16, 1991, which is a continuation-in-part of Ser. No. 07/455,080 (U.S. Pat. No. 5,089,603) filed Dec. 22, 1989, which is a continuation-in-part of Ser. No. 07/369,479 (U.S. Pat. No. 5,079,344), filed Jun. 21, 1989. This application is also a continuation-in-part of U.S. application Ser. No. 08/180,145, (pending) filed Jan. 11, 1994, which is continuation-in-part of U.S. application Ser. No. 08/137,253 (pending), filed Oct. 14, 1993, which is a continuation-in-part of U.S. application Ser. No. 08/090,527 (U.S. Pat. No. 5,342,924), filed Jul. 9, 1993, which is a continuation-in-part of U.S. application Ser. No. 07/973,321 (U.S. Pat. No. 5,254,671), filed Oct. 29, 1992, which is a continuation-in-part of U.S. application Ser. No. 07/515,604 (U.S. Pat. No. 5,274,075), filed Apr. 27, 1990, which is a continuation-in-part of U.S. application Ser. No. 07/468,766 (U.S. Pat. No. 5,260,416), filed Jan. 23, 1990, which is a continuation-in-part of U.S. application Ser. No. 07/369,625 (abandoned), filed Jun. 21, 1989, which is a continuation-in-part of U.S. application Ser. No. 07/272,243 (U.S. Pat. No. 5,091,313), filed Nov. 16, 1988, which is a continuation-in-part of U.S. application Ser. No. 07/229,178 (abandoned), filed Aug. 5, 1988, which is a continuation-in-part of U.S. application Ser. No. 07/226,421 (U.S. Pat. No. 5,422,258), filed Jul. 29, 1988, which is a continuation-in-part of U.S. application Ser. No. 07/140,036 (abandoned) filed Dec. 31, 1987.

FIELD OF THE INVENTION

The invention includes peptides relating to epitopes present on B cell-bound but not secreted IgA.

BACKGROUND OF THE INVENTION

B lymphocytes produce five classes of immunoglobulins, each of which mediates different functions. IgM is most effective in complement fixation, IgG causes opsonization and cellular cytotoxicity and can cross the placenta. IgA functions on the mucosal surface and IgE mediates degranulation of mast cells and basophils. The function of IgD is still not well understood. These antibodies are present in the blood circulation, with IgG, IgA, and IgM being the major serum components.

In addition to secreting immunoglobulins, the B cells also express different isotypes of the immunoglobulins on their cell surfaces at different stages of maturation. IgM and IgD are present on the surface of resting, uncommitted B cells. Often only one of the five classes of immunoglobulins exists on late stage, mature B cells, which secrete the same immunoglobulin isotype as expressed on their cell surface. Teale, J. M., et al., *J. Immunol.* 1126: 1952–1957 (1981); Gathings, W. E., et al., *Immunol. Rev.* 57: 107–126 (1981); Teale, J. M., *Fed. Proc.* 41: 5–9 (1982).

Numerous pathogenic microorganisms, such as bacteria and viruses, enter the body through the respiratory, gastrointestinal, and genitourinary tracts during air inhalation, food and liquid intake, and sexual contact. The potentially allergenic substances, e.g., tree, grass, and flower pollens, dust mites, fungal particles and animal dander, also enter the body through the respiratory tract. IgA is produced by plasma cells located along the mucosal linings of the aforementioned tracts, which are all exposed to the external environment. The $\alpha$ chain and light chain immunoglobulins produced by plasma cells combine with a secretory component produced by the epithelial cells in the mucosal tissues, forming secretory IgA molecules that are secreted to the surface of mucosal layers. See generally J. G. Nedrud et al., "Adjuvants and the Mucosal Immune System", *Topics in Vaccine Adjuvant Research*, (Spiggs, D. E., Koff, W. C., Eds.) CRC Press, Boca Raton, Fla. (1990). These secretory IgA molecules bind to the invading pathogens and weaken their ability to penetrate the mucosal layer and to enter the inner tissue and blood stream of the host. See generally J. G. Nedrud et al., "Adjuvants and the Mucosal Immune System", *Topics in Vaccine Adjuvant Research*, (Spiggs, D. E., Koff, W. C., Eds.) CRC Press, Boca Raton, Fla. (1990). IgA can also bind allergenic substances, thereby preventing the allergens from triggering allergic reactions.

It has been found that individuals with low IgA production are more prone to various infectious diseases and have a higher tendency to develop allergic diseases than those with normal IgA levels. Thus, if the levels of either total IgA or antigen-specific IgA can be increased, diseases and allergies may be prevented.

It is also well known that various allergenic substances enter through inhalation and food ingestion, causing immediate-type, antibody-mediated hypersensitivities and delayed-type, cell-mediated hypersensitivities. In sensitized individuals, the IgE-mediated reactions against pollens, animal danders, dust mites, and other allergenic antigens cause the common allergic symptoms such as allergic rhinitis ("hay fever") and extrinsic asthma. In such allergic responses, the allergens enter the mucosal layers of the respiratory tracts and nasal linings and bind to allergen-specific IgE which is on the surface of basophils and mast cells. The binding of IgE by the allergens on the basophils and mast cell surface causes cross-linking of the underlying IgE Fc receptors, and triggers the release of histamines and other pharmacologic mediators, resulting in various allergic symptoms. In cell-mediated hypersensitivities, certain T helper cells responsible for delayed-type hypersensitivity are activated. These T cells recruit and activate macrophages, causing inflammatory symptoms.

It has been shown that antibodies which bind to epitopes of B cell membrane-bound immunoglobulins can be used to eliminate B cells producing the immunoglobulins. Similarly, antibodies specific for the antigenic epitope located on the transmembrane anchoring peptide of B cell membrane-bound (but not secreted) IgA can be used for removing IgA secreting B cells. Such antibodies could be useful in treating B cell leukemias or lymphomas, as these malignancies are monoclonal, and therefore, only B cells producing the IgA isotype will be affected. Such antibodies could also be useful for treating IgA nephropathy, where IgA mediates the disease. As an alternative, it would also be possible to generate such antibodies endogenously, through the use of a peptide vaccine with a sequence corresponding to the extracellular segment of B cell membrane-bound IgA.

SUMMARY OF THE INVENTION

The invention includes peptides representing the extracellular segment of the membrane anchoring peptide of human α chain, oligonucleotides coding therefore, antibodies and related products to epitopes on this extracellular segment, prophylactic and therapeutic treatments involving such peptides, antibodies and related products, and their use in diagnostic assays. These extracellular peptide segments form, entirely or in part, antigenic epitopes unique to membrane-bound but not secreted IgA.

Membrane-bound human IgA has two subclasses, α1 and α2, and two isoforms, a longer and a shorter isoform. The membrane anchoring extracellular peptide segment for the longer isoform of human α1 has the amino acid sequence:

Gly Ser Cys Ser Val Ala Asp Trp Gln Met Pro Pro Pro Tyr Val Val Leu Asp Leu Pro Gln Glu Thr Leu Glu Glu Glu Thr Pro Gly Ala Asn (SEQ ID NO:1).

The sequence of the membrane anchoring extracellular peptide segment for the longer isoform of human α2 is the same except that the fourth Serine residue is substituted with a Cysteine.

The membrane anchoring extracellular peptide segment for the shorter isoform of human α1 and α2 both have the same amino acid sequence:

Asp Trp Gln Met Pro Pro Pro Tyr Val Val Leu Asp Leu Pro Gln Glu Thr Leu Glu Glu Glu Thr Pro Gly Ala Asn (SEQ ID NO:2).

Peptides including these sequences or immunologically equivalent sequences (or a epitope thereof) can be conjugated to protein carriers and used to induce formation of endogenous antibodies to these unique extracellular epitopes of human IgA. These endogenously produced antibodies can deplete IgA-producing B cells if provided with the proper effector function. Alternatively, these peptides can be used to generate antibodies (polyclonal or monoclonal) targeting the membrane anchoring extracellular peptide segment of IgA, which antibodies can be used to assay for IgA-producing B cells in a cell population, or for other diagnostic or assay uses. Nucleotides coding for these peptides can be used with well-known recombinant techniques to generate these peptides.

DETAILED DESCRIPTION OF THE INVENTION AND ITS MANNER AND PROCESS OF MAKING AND USING

1. The Exposed Extracellular Domains of the Membrane Anchoring Peptides of Membrane-bound Immunoglobulins The membrane-bound immunoglobulins expressed on the surface of B cells differ from the secretory immunoglobulins synthesized by the same cells in that the former have extra peptidic segments extending from the C-termini of the immunoglobulin heavy chains which anchor the immunoglobulins to the cell surface. The extracellular portions of these extra segments are unique for different isotypes and are referred to herein as the membrane anchoring peptides.

The amino acid sequence data of the eleven membrane-bound immunoglobulins from several species have been determined. See Word, C. J. et al., *EMBO J.* 2: 887–898 (1983); Ishida, N. et al., *EMBO J.*, 1: 1117–1123 (1982); Steen, M. L..et al., *J. Mol. Biol.*, 177: 19–32 (1984); Rogers, J. et al., *Cell*, 26: 19–27 (1981); Yamawaki-Kataoka, Y. et al., *Proc. Nat'l. Acad. Sci.*, USA, 79: 2008–2012 (1982); Kamaromy, M. et al., *Nucleic Acids Res.*, 11: 6775–6785 (1983); Rogers, J. et al., *Cell*, 20: 303–312 (1980); Bernstein, K. E., *J. Immunol.* 132: 490–495 (1984); Cheng, H. et al., *Nature*, 296: 410–415 (1982); Rabbitts, T. H. et al., *Nucleic Acids Res.* 9: 4509–4524. These sequences indicate certain common features of the membrane anchoring peptides. As shown in Table 1, the membrane anchoring peptide has three segments which are distinguishable based upon their locations in relation to the plasma membrane. Even though these peptides are short, ranging from 41 to 130 amino acid residues, and have often been referred to as the "membrane-bound domain," the peptides are not entirely in the membrane lipid bilayer. In fact, only 25 amino acid residues, which are largely hydrophobic residues and also the threonine and serine residues which are located in the middle part of the peptides, are in the lipid bilayer. The C-terminal, hydrophilic segments of 3 to 28 amino acid residues are located on the cytoplasmic side of the membrane. The segments toward the N-terminus, which are connected to the third or fourth constant domains of the immunoglobulin heavy chains ($CH_3$ or $CH_4$) are very hydrophilic and are on the extracellular side of the plasma membrane.

TABLE 1

Key Features and Properties of Peptide Segments Unique to Membrane-Bound Immunoglobulins.

| Immuno-globulin Class/Subclass | First Segment | Middle Segment | Last Segment | Total |
|---|---|---|---|---|
| | Length # Amino Acid Residues | | | |
| Mouse IgA | 26 | 25 | 14 | 65 |
| Mouse IgE | 19 | 25 | 28 | 72 |
| Rat IgE | 19 | 25 | 28 | 72 |
| Mouse IgG$_1$ | 18 | 25 | 28 | 71 |
| Mouse IgG$_{2a}$ | 18 | 25 | 28 | 71 |
| Mouse IgG$_{2b}$ | 18 | 25 | 28 | 71 |
| Mouse IgG$_3$ | 18 | 25 | 28 | 71 |
| Mouse IgM | 13 | 25 | 3 | 41 |
| Human IgM | 13 | 25 | 3 | 41 |
| Human IgD | 27 | 25 | 3 | 55 |
| Mouse IgD | 26 | 25 | 3 | 54 |
| Properties | Hydrophilic Highly Acidic | Hydrophobic No Charged Residues | Hydrophilic | |
| Physical Location | On Exterior Surface | In Membrane Lipid Bilayer | On Cytoplasmic Surface | |
| Abbreviated Symbols | mb/ec Segment | mb/tm Segment | mb/ic Segment | |

* mb stands for membrane-bound; ec for extracellular; tm for transmembrane; and ic for intracellular.

The shortest extracellular segments of the membrane-bound pieces of the immunoglobulins (designated mb/ec segments) have 13 amino acid residues (mouse and human μ chains). The mb/ec segments of all immunoglobulins contain high proportions of charged, acidic, amino acid residues. The charged amino acid residues and polar hydrophilic residues account for a very high percentage of the amino acids in the mb/ec segment. This indicates that all the mb/ec segments are exposed and of sufficient length to be accessible by antibodies.

2. Developing Antibodies to the mb/ec Segment

The α.mb/ec peptides of the invention can be used in the immunization of animals to prepare polyclonal and monoclonal antibodies. They can also be used to screen for specific monoclonal antibodies or characterize specific polyclonal antibodies. They can also be used to purify monoclonal and polyclonal antibodies. The nucleotides encoding the peptides can be used, in conventional recombinant processes, to make the peptides. The production of the peptides can be done in a bacterial or mammalian host cell line. Alternatively, the peptides can be synthesized with the RAMPs system, or with a peptide synthesizer.

In the process of preparing monoclonal antibodies specific for α.mb/ec peptides it is not necessary to use the synthetic or recombinant α.mb/ec peptides in both immunization and antibody identification. For example, in immunizing mice for preparing immune spleen cells for fusion with myeloma cells, the immunogen may be the membrane-bound IgA isolated from plasma membrane of IgA-bearing myeloma cells, such as DAKIKI lymphoblastoid cells, or it may be the IgA-bearing myeloma cells themselves. Transfectomas, developed by transfecting mouse myeloma cells with genes of human immunoglobulin heavy chains and light chains which express on their cell surface membrane-bound immunoglobulin, may also be used as immunogens. For initial monoclonal antibody identification following immunization, the aforementioned synthetic peptide conjugated to bovine serum albumin or ovalbumin with the techniques described below are preferably used.

When using the synthetic or recombinant α.mb/ec peptides as immunogens, it is more effective to conjugate them to a protein carrier, for example, hepatitis B surface antigen, core antigen, or preferably, keyhole limpet hemocyanin (KLH). If the peptidic segment lacks a Lysine residue or if the Lysine residue is in the middle part of the segment, it is desirable to add a Lysine residue at the C-terminal end. Because the N-terminus already has an α-amino group, the modified synthetic peptidic will then have two amino groups for linking.

Multiple molecules of peptides can be conjugated to each molecule of the carrier protein. With KLH, a preferred molar ratio for peptide/KLH is 10. The method of conjugation is well established. Cross-linkers such as his (sulfosuccinimidyl) suberate or disulfosuccinimidyl tartarate (Catalogue #21579, 20591, Pierce Chemical Co., Rockford, Ill.), or preferably gluteraldehyde, can be used.

The immunogen, e.g. the KLH conjugate, can be used to immunize rabbits, goats, rats, or mice to prepare polyclonal antibodies specific for the α.mb/ec peptide. Lymphocytes from the spleen or lymph nodes of immune mice and rats can also be taken to prepare hybridomas secreting monoclonal antibodies specific for the α.mb/ec peptide. A preferred protocol to prepare the monoclonal antibodies is to fuse immune spleen cells of mice with non-secreting mouse myeloma cells, such as NS-1 or SP2/0 cells, using polyethylene glycol.

A preferred immunization procedure for mice is to prime each mouse by injecting 50 μg of the peptide-KLH conjugate in complete Fruend's adjuvant subcutaneously into each mouse. Two and four weeks later, the same amounts of antigen are given subcutaneously in incomplete Freund's adjuvant. After about six weeks, the fourth antigen injection is given intraperitoneally in saline. Mice are sacrificed 4 days after the last injection and the spleens are removed for preparing single cell suspension for fusion with myeloma cells.

A similar protocol can also be used for immunization with other immunogens. For example, a similar protocol can be used where the immunogen is purified native human membrane-bound IgA (having an attached membrane anchoring peptide) isolated from the plasma membrane of IgA-bearing human myeloma cells, such as DAKIKI lymphoblastoid cells, or where the immunogen is recombinant α chain produced by genetically engineered bacteria.

The fusion procedure with polyethylene glycol and other various procedures concerning cloning and hybridoma culturing have been well established. The preferred protocol is the well-known one described, for example, by Hudson, L. and Hay. F. C. (Practical Immunology, 2nd edition, pp. 303-313, 1980, Blackwell Publishing Co., Boston).

The screening of hybridomas for monoclonal antibodies (or the identification of polyclonal antibodies) reactive with α.mb/ec peptide can be performed with an enzyme linked immunosorbent assay (ELISA) using the synthetic or recombinant α.mb/ec peptide as the solid phase antigen. An alternative solid phase antigen is the conjugate of α.mb/ec peptide with a carrier protein different from that used as the immunogen, such as ovalbumin or bovine serum albumin.

Further characterization of the monoclonal and polyclonal antibodies is shown in Table 2. The assays employed in these studies are also indicated.

TABLE 2

The Reactivity of Antibodies Specific for the α.mb/ec Peptide with Different IgA-Containing Targets

| | Reactivity | Assays |
|---|---|---|
| Synthetic α.mb/ec peptide | + | ELISA |
| Soluble IgA | − | ELISA |
| DAKIKI myeloma cells | + | Immunofluorescence staining |
| IgA-bearing B cells | + | Immunofluorescence staining |
| Cells not expressing surface IgA | − | Immunofluorescence staining |

3. Application of α.mb/ec Peptide for Treating Diseases

The α.mb/ec peptides can be used therapeutically to decrease secretory IgA or IgA-bearing B cells. Even though human α.mb/ec peptide is probably not immunogenic in humans, synthetic or recombinant peptides with the same sequence, or immunological equivalents, can be linked to carrier proteins, such as hepatitis B surface antigen core antigen, or KLH, and become immunogenic and capable of inducing antibodies that cross-react with the authentic α.mb/ec epitope. The preferred synthetic or recombinant peptides have the amino acid sequence shown in SEQ ID NO:1 (α1 subclass, as shown, or α2 subclass, with a cysteine substituted for the fourth serine in the α1 subclass peptide), SEQ ID NO:2, or immunological equivalents thereof.

A nucleotide sequence coding for the peptide of SEQ ID NO:1 is shown in SEQ ID NO:3. A nucleotide sequence coding for the peptide of SEQ ID NO:2 is the same as that for SEQ ID NO:1, except that it does not include the first 18 nucleotides of SEQ ID NO:1. A number of other nucleotides (including mRNAs) can also code for the peptides of the invention.

These α.mb/ec peptide conjugates can be administered to patients with over-production of IgA or excess IgA-bearing B cells, such as exists in lymphoma and IgA nephropathy.

4. Diagnostic Uses

Antibodies against α.mb/ec epitopes can be used for determining numbers and relative proportions of IgA-bearing lymphocytes in mixed leukocyte populations. The α.mb/ec-specific antibodies will not react with cells which bear secreted immunoglobulins on the cells' Fc receptors. Such cells include macrophages and activated T cells. The profile of the IgA-bearing B cells may indicate the immune status of the individual. The same information can indicate how much antibody should be administered to cause proliferation of IgA-expressing B cells. For this purpose, antibodies can be used in standard assay formats which are used to determine cell surface antigens. In general, the antibody is contacted with a sample of the leukocytes to be tested under conditions which allow the antibody to bind IgA-bearing cells in the sample. The cells are then examined for binding of antibody. This can be accomplished by conventional cell staining procedures, for example, a fluorescently labeled second antibody can be used to detect binding of the anti-IgA antibody.

As noted above, the peptides of the invention can be used to make such antibodies, and the nucleotides of the invention which code for the peptides can be used to produce the peptides.

EXAMPLE I

Determining the Sequence of α.mb/ec Peptide

Materials and Methods

DNA library and probe. The human genomic DNA library was purchased from Stratagene (La Jolla, Calif.). This library was constructed using genomic DNA from human lung fibroblast line, WI38, packaged in phage FIX. A 30-base oligonucleotide (SEQ ID NO:4) which corresponds to a segment located in the CH3 coding region of immunoglobulin allotype α1 and α2, was synthesized and used as a probe to screen phage clones containing either oil and α2 gene segments using in situ hybridization.

Polymerase chain reaction (PCR). To amplify genomic DNA segments, the purified DNA from the positive clones was used as the templates. One primer was a 17-base oligonucleotide, SEQ ID NO:5, located in the intron about 1 kb down-stream from CH3 exon, and the other primer was a 21-base oligonucleotide, SEQ ID NO:6, which is a very conservative segment in the published mouse α membrane exon (Word et al. *EMBO J.* 2: 887,1983). To amplify cDNA spanning human CH3 and the membrane exon, purified cDNA reverse transcribed from mRNA from a surface IgA-expressing cell line (see below) was used as the template. One primer was the same 30-base oligonucleotide (SEQ ID NO:4) located in CH3 exon used in genomic library screening, and the other primer was an 18-base oligonucleotide, SEQ ID NO:7, which is located at the junction of human α membrane exon and the 3' untranslated region. The PCR was carried out in DNA Thermal Cycler (Perkin Elmer Cetus) and the reaction conditions were: denaturing at 94° C. for 1 minute, annealing at 50° C. for 2 minutes, reacting with Taq polymerase (Perkin Elmer Cetus) at 72° C. for 5 minutes with genomic DNA, or 45 seconds for cDNA. The reaction cycles were 30 for genomic DNA and 40 for cDNA.

Cloning and sequencing. The products from PCR were extracted with phenol. The newly synthesized DNA segments were blunted by Mung Bean nuclease (United States Biochemicals) and their 5' ends were phosphorylated by polynucleotide kinase (New England Biolabs). The amplified DNA fragments of interest were isolated by agarose gel electrophoresis and ligated into plasmid pUC19 (United States Biochemicals) at the restriction site of Sma 1. After transforming into *E. coli* DH5α (Bethesda Research Laboratories), the amplified plasmids were purified using CIRCLEPREP kit (BIO101). DNA sequences of the inserts were determined by dideoxy sequencing on double stranded DNA with a T7 Sequencing Kit (Pharmacia). The membrane exon regions were sequenced on both strands of DNA to minimize errors. An additional step was performed for identifying clones containing inserts of α gene segment amplified by PCR from cDNA. The colonies were hybridized with an oligonucleotide probe of 22 nucleotides (SEQ ID NO:8) located between the two primers used in PCR.

Southern blot and subclone. As described above, the first genomic DNA segment used for sequencing was obtained by PCR amplification using two primers, the 3'-end primer of which was in the middle of the membrane exon. In order to obtain sequences for the remaining 3'-end of the membrane exon and the 3' untranslated region, gene segments containing these regions were prepared. Purified genomic DNA's from clones containing human α1 and α2 segments were digested with restriction enzyme Ava 1, electrophoresed on 1% agarose gel, and blotted onto a nitrocellulose filter according to the standard Southern blot method. A $^{32}$P labelled oligonucleotide located in the membrane exon mentioned above (SEQ ID NO:8) was used as a probe to identify DNA fragments containing segments neighboring the oligonucleotide probe. The positive segments were then isolated and subcloned into pUC 19 at the restriction site Ava 1 and sequenced downstream using the same oligonucleotide used in Southern blot analysis.

RNA and cDNA preparation. A mIgA-expressing cell line, DAKIKI (ATCC TIB206), was used as the source of mRNA. About 5×10$^7$ cells were harvested for isolation of total RNA using the Guanidinium procedure. With the purified RNA as the template and an oligonucleotide at the end of membrane exon as the primer (SEQ ID NO:7), the first strand cDNA was polymerized by the reverse transcriptase AMV (Life Science, Inc.) according to the procedure in the provided instruction manual.

RESULTS

PCR Amplification of α1 and α2 Gene Segments from Genomic DNA and Their Nucleotide Sequences Nine phage lambda clones containing human α1 and α2 heavy chain gene segments were identified from the human genomic library. These clones were used directly as the template for PCR with SEQ ID NO:5 and SEQ ID NO:6 as primers. The 5' end primer (SEQ ID NO:5) for the PCR was selected from a segment identical between human α1 and α2 genes located near the 3' end of the published genomic DNA sequences, which ends in an intron about 1.1 kb downstream from CH3. Flanagen, J. G., et al. *Cell* 36: 681–688 (1984). Whether the genes belong to α1 or α2 subclass can be distinguished by subclass-specific sequences immediately downstream from the SEQ ID NO:5 primer. Both α1 and α2 membrane gene segments were identified among the nines lambda genomic clones. Through agarose gel electrophoresis, the products of PCR were separated into 3 bands of DNA segments, 2 major bands of 1.8 kb and 300 bp, respectively, and a minor band of 2.2 kb. The 1.8 kb segment was thought the segment of interest judging by the size of the corresponding segment in the already sequenced murine α gene. This DNA segment was purified from the agarose gel, subcloned, and sequenced.

The sequence of this 1.8 kb fragment indicated that on its 3' end there was a segment of about 120 bp with a sequence which was very homologous with that of a murine α membrane exon. A possible splicing acceptor sequence (SEQ ID NO:9) was identified near the 5' end of this 120 bp segment. Since the 1.8 kb fragment ends in the middle of the membrane exon, the sequences for the remaining membrane exon and the 3' untranslated region were obtained by subcloning and sequencing of additional lambda clones containing segments flanking the membrane exons. These clones were identified by Southern blot analysis using a probe (SEQ ID NO:8) from the membrane exon.

The sequence of the membrane exon (194 bp) and about 1,700 bp of 5' flanking sequence and about 500 bp in the 3' untranslated region of α1 subclass indicates that the stop codon TGA is at exactly the same site as that of a murine α membrane exon, indicating that human and mouse a membrane exons are both of 194 nucleotides in length. At about 400 bp downstream from the membrane exon, there is a possible mRNA termination and polyadenylation signal sequence, SEQ ID NO:10. Like the murine a gene, the human α genes have only one membrane exon, while all other classes of human or murine heavy chain genes with known sequences have two membrane exons. The intron between CH3 and the membrane exon has 2,579 bp, somewhat longer than the 2,350 bp of murine. In this intron, there is a region of about 630 bp in which only a few C bases and more than 20 repeated sequences of SEQ ID NO:11 and other repeated sequences exist. The significance of this is unknown.

PCR and DNA sequencing on cDNA. As mentioned above, the human α membrane exon was located by comparing the sequence of the segment amplified from genomic DNA with that of murine α membrane exon as well as by searching for the splicing acceptor consensus sequence. A segment of 194 nucleotides was originally thought to be the membrane exon. To confirm this, isolation of the total RNA from a human mIgA-expressing cell line, DAKIKI, was performed, and its cDNA was prepared. With this cDNA as a template, a segment spanning CH3 and the membrane exon was amplified by PCR. Although the PCR cycles were increased from 30 to 40, the efficiency of amplification was still not as good as that of PCR on genomic DNA, probably because of the relative lower proportion of the specific template of interest in the cDNA prepared from the total RNA. On agarose gel electrophoresis, the PCR products displayed a weak band of the right size with a heavy smear around it. This band was cut out and subcloned. To help in identifying the specific clones, in situ colony hybridization was performed using a probe located between the two primers of PCR. Positive clones were picked up and purified and sequenced, using the same method as that used for the genomic DNA sequencing.

The results showed that them were clones containing DNA inserts which correspond to two species of mRNA of human membrane-bound α1. The two mRNA species resulted from the use of two different splicing acceptor sites: one from the predicted site, SEQ ID NO:12 (a corresponding site for which exists in the murine α gene); and one from an acceptor site, SEQ ID NO:13, 18 nucleotides upstream in the same reading frame, for which there is no corresponding site in the murine α gene. The two mRNA species would yield two membrane-bound α1 polypeptides, one with 65 amino acid residues (SEQ ID NO:14) and the other with 71 amino acid residues (SEQ ID NO:15) in the membrane anchoring peptide region. These two mRNA species and their corresponding peptides are referred to as isoforms.

The proposed extracellular segments of the membrane anchoring peptides of these two isoforms are respectivity either 26 or 32 amino acid residues in length (designated α.mb/ec peptides). These segments are proposed to be extracellular based on the fact that they contain high proportions of acidic residues. These α.mb/ec segments are the target antigenic epitopes for antibody or peptide-based treatments, and are the first 26 amino acids in SEQ ID NO:14 and the first 32 amino acids in SEQ ID NO:15.

SEQ ID NO:16 shows the amino acid sequence of the shorter isoform (the first 26 amino acids representing the α.mb/ec segment) of human α2, and SEQ ID NO:17 shows the amino acid sequence of the longer isoform (the first 32 amino acids representing the α.mb/ec segment) of human α2. SEQ ID NO:18 shows the amino acid sequence of the murine α membrane exon.

It can be seen that human α1 and α2 are highly homologous to murine α. Further, the human α.mb/ec peptides are identical between α1 and α2 for the shorter isoform and are only one amino acid residue different (at the fourth position) for the longer isoform.

EQUIVALENTS

Those skilled in the art will recognize, or be able to ascertain using no more than routine experimentation, many equivalents to the specific embodiments of the invention described above. Such equivalents are encompassed by the following claims.

What is claimed is:

1. A peptide having the sequence of the peptide shown in SEQ ID NO:1.

2. The peptide of claim 1 wherein a cysteine is substituted for the serine which is the fourth amino acid from the N-terminal end.

3. A peptide having the sequence of the peptide shown in SEQ ID NO:2.

4. The peptide of any of claims 1 to 3 conjugagted to a carrier protein.

5. The peptide of claim 4 wherein the carrier protein is keyhole limpet hemocyanin.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
　　　　　　　( A ) LENGTH: 32
　　　　　　　( B ) TYPE: amino acid
　　　　　　　( D ) TOPOLOGY: linear ( x i ) SEQUENCE DESCRIPTION: SEQ ID NO:1:

```
Gly Ser Cys Ser Val Ala Asp Trp Gln Met Pro Pro Pro Tyr Val
1               5                   10                  15

Val Leu Asp Leu Pro Gln Glu Thr Leu Glu Glu Glu Thr Pro Gly Ala Asn
                20                  25                  30
```

( 2 ) INFORMATION FOR SEQ ID NO:2:

( i ) SEQUENCE CHARACTERISTICS:

(A) LENGTH: 26
(B) TYPE: amino acid
(D) TOPOLOGY: linear (xi) SEQUENCE DESCRIPTION: SEQ ID NO:2:

```
Asp Trp Gln Met Pro Pro Tyr Val Val Leu Asp
 1           5                   10
Leu Pro Gln Glu Thr Leu Glu Glu Thr Pro Gly
         15                  20
Ala Asn
 25
```

(2) INFORMATION FOR SEQ ID NO:3:

(i) SEQUENCE CHARACTERISTICS:
(A) LENGTH: 96
(B) TYPE: Nucleic acid
(C) STRANDEDNESS: double
(D) TOPOLOGY: Linear (xi) SEQUENCE DESCRIPTION: SEQ ID NO:3:

```
GGC TCT TGC TCT GTT GCA GAT TGG CAG ATG CCG CCT CCC TAT GTG GTG  48
Gly Ser Cys Ser Val Ala Asp Trp Gln Met Pro Pro Pro Tyr Val Val
 1               5                   10                  15

CTG GAC TTG CCG CAG GAG ACC CTG GAG GAG GAG ACC CCC GGC GCC      93
Leu Asp Leu Pro Gln Glu Thr Leu Glu Glu Glu Thr Pro Gly Ala
                 20                  25                  30

AAC  96
Asn
```

(2) INFORMATION FOR SEQ ID NO:4:

(i) SEQUENCE CHARACTERISTICS:
(A) LENGTH: 30
(B) TYPE: nucleic acid
(C) STRANDEDNESS: Double
(D) TOPOLOGY: Linear (xi) SEQUENCE DESCRIPTION: SEQ ID NO:4:

GCGAGAAGTA CCTGACTTGG GCATCCCGGC  30

(2) INFORMATION FOR SEQ ID NO:5:

(i) SEQUENCE CHARACTERISTICS:
(A) LENGTH: 17
(B) TYPE: nucleic acid
(C) STRANDEDNESS: Double
(D) TOPOLOGY: Linear (xi) SEQUENCE DESCRIPTION: SEQ ID NO:5:

CTGCCTGGC CAAGTCTC  17

(2) INFORMATION FOR SEQ ID NO:6:

(i) SEQUENCE CHARACTERISTICS:
(A) LENGTH: 21
(B) TYPE: nucleic acid
(C) STRANDEDNESS: Double
(D) TOPOLOGY: Linear (xi) SEQUENCE DESCRIPTION: SEQ ID NO:6:

GAACAAGCTC AGTAGGAAGA G  21

(2) INFORMATION FOR SEQ ID NO:7:

(i) SEQUENCE CHARACTERISTICS:

(A) LENGTH: 18
        (B) TYPE: nucleic acid
        (C) STRANDEDNESS: Double
        (D) TOPOLOGY: Linear (xi) SEQUENCE DESCRIPTION: SEQ ID NO:7:

GCTCCCGCTC AGTACTGG 18

(2) INFORMATION FOR SEQ ID NO:8:

(i) SEQUENCE CHARACTERISTICS:
        (A) LENGTH: 22
        (B) TYPE: nucleic acid
        (C) STRANDEDNESS: Double
        (D) TOPOLOGY: Linear (xi) SEQUENCE DESCRIPTION: SEQ ID NO:8:

CCTCCCTATG TGGTGCTGGA CT 22

(2) INFORMATION FOR SEQ ID NO:9:

(i) SEQUENCE CHARACTERISTICS:
        (A) LENGTH: 7
        (B) TYPE: nucleic acid
        (C) STRANDEDNESS: Double
        (D) TOPOLOGY: Linear (xi) SEQUENCE DESCRIPTION: SEQ ID NO:9:

TTGCAGA 7

(2) INFORMATION FOR SEQ ID NO:10:

(i) SEQUENCE CHARACTERISTICS:
        (A) LENGTH: 6
        (B) TYPE: nucleic acid
        (C) STRANDEDNESS: Double
        (D) TOPOLOGY: Linear (xi) SEQUENCE DESCRIPTION: SEQ ID NO:10:

AATAAA 6

(2) INFORMATION FOR SEQ ID NO:11:

(i) SEQUENCE CHARACTERISTICS:
        (A) LENGTH: 7
        (B) TYPE: nucleic acid
        (C) STRANDEDNESS: Double
        (D) TOPOLOGY: Linear (xi) SEQUENCE DESCRIPTION: SEQ ID NO:11:

GGATGGA 7

(2) INFORMATION FOR SEQ ID NO:12:

(i) SEQUENCE CHARACTERISTICS:
        (A) LENGTH: 7
        (B) TYPE: nucleic acid
        (C) STRANDEDNESS: Double
        (D) TOPOLOGY: Linear (xi) SEQUENCE DESCRIPTION: SEQ ID NO:12:

TTGCAGA 7

(2) INFORMATION FOR SEQ ID NO:13:

(i) SEQUENCE CHARACTERISTICS:
        (A) LENGTH: 7
        (B) TYPE: nucleic acid (C) STRANDEDNESS: Double
(D) TOPOLOGY: Linear (xi) SEQUENCE DESCRIPTION: SEQ ID NO:13:

TGGCAGG 7

(2) INFORMATION FOR SEQ ID NO:14:

(i) SEQUENCE CHARACTERISTICS:
(A) LENGTH: 65
(B) TYPE: amino acid
(D) TOPOLOGY: Linear (xi) SEQUENCE DESCRIPTION: SEQ ID NO:14:

```
Asp Trp Gln Met Pro Pro Pro Tyr Val Val Leu Asp Leu Pro Gln Glu Thr
1               5                   10                  15

Leu Glu Glu Glu Thr Pro Gly Ala Asn Leu Trp Pro Thr Thr Ile Thr Phe
        20                  25                  30

Leu Thr Leu Phe Leu Ile Ser Leu Phe Tyr Ser Thr Ala Leu Thr Val Thr
35                  40                  45                  50

Ser Val Arg Gly Pro Ser Gly Asn Arg Glu Gly Pro Gln Tyr
            55                  60                  65
```

(2) INFORMATION FOR SEQ ID NO:15:

(i) SEQUENCE CHARACTERISTICS:
(A) LENGTH: 71
(B) TYPE: amino acid
(D) TOPOLOGY: Linear (xi) SEQUENCE DESCRIPTION: SEQ ID NO:15:

```
Gly Ser Cys Ser Val Ala Asp Trp Gln Met Pro Pro Pro Tyr Val Val Leu
1               5                   10                  15

Asp Leu Pro Gln Glu Thr Leu Glu Glu Glu Thr Pro Gly Ala Asn Leu Trp
        20                  25                  30

Pro Thr Thr Ile Thr Phe Leu Thr Leu Phe Leu Ile Ser Leu Phe Tyr Ser
35                  40                  45                  50

Thr Ala Leu Thr Val Thr Ser Val Arg Gly Pro Ser Gly Asn Arg Glu Gly
            55                  60                  65

Pro Gln Tyr
        70
```

(2) INFORMATION FOR SEQ ID NO:16:

(i) SEQUENCE CHARACTERISTICS:
(A) LENGTH: 65
(B) TYPE: amino acid
(D) TOPOLOGY: Linear (xi) SEQUENCE DESCRIPTION: SEQ ID NO:16:

```
Asp Trp Gln Met Pro Pro Pro Tyr Val Val Leu Asp Leu Pro Gln Glu Thr
1               5                   10                  15

Leu Glu Glu Glu Thr Pro Gly Ala Asn Leu Trp Pro Thr Thr Ile Thr Phe
        20                  25                  30

Leu Thr Leu Phe Leu Ile Ser Leu Phe Tyr Ser Thr Ala Leu Thr Val Thr
35                  40                  45                  50

Ser Val Arg Gly Pro Ser Gly Lys Arg Glu Gly Pro Gln Tyr
            55                  60                  65
```

(2) INFORMATION FOR SEQ ID NO:17:

(i) SEQUENCE CHARACTERISTICS:

(A) LENGTH: 71
(B) TYPE: amino acid
(D) TOPOLOGY: Linear (xi) SEQUENCE DESCRIPTION: SEQ ID NO:17:

| Gly | Ser | Cys | Cys | Val | Ala | Asp | Trp | Gln | Met | Pro | Pro | Pro | Tyr | Val | Val | Leu |
|---|---|---|---|---|---|---|---|---|---|---|---|---|---|---|---|---|
| 1 | | | 5 | | | | | | 10 | | | | | 15 | | |

| Asp | Leu | Pro | Gln | Glu | Thr | Leu | Glu | Glu | Glu | Thr | Pro | Gly | Ala | Asn | Leu | Trp |
|---|---|---|---|---|---|---|---|---|---|---|---|---|---|---|---|---|
| | | 20 | | | | | 25 | | | | | 30 | | | | |

| Pro | Thr | Thr | Ile | Thr | Phe | Leu | Thr | Leu | Phe | Leu | Ile | Ser | Leu | Phe | Tyr | Ser |
|---|---|---|---|---|---|---|---|---|---|---|---|---|---|---|---|---|
| 35 | | | | | 40 | | | | | 45 | | | | | 50 | |

| Thr | Ala | Leu | Thr | Val | Thr | Ser | Val | Arg | Gly | Pro | Ser | Gly | Lys | Arg | Glu | Gly |
|---|---|---|---|---|---|---|---|---|---|---|---|---|---|---|---|---|
| | | | 55 | | | | | 60 | | | | | 65 | | | |

| Pro | Gln | Tyr |
|---|---|---|
| | 70 | |

(2) INFORMATION FOR SEQ ID NO:18:

(i) SEQUENCE CHARACTERISTICS:
(A) LENGTH: 65
(B) TYPE: amino acid
(D) TOPOLOGY: Linear (xi) SEQUENCE DESCRIPTION: SEQ ID NO:18:

| Glu | Arg | Gln | Glu | Pro | Leu | Ser | Tyr | Val | Leu | Leu | Asp | Gln | Ser | Gln | Asp | Thr |
|---|---|---|---|---|---|---|---|---|---|---|---|---|---|---|---|---|
| 1 | | | | 5 | | | | | 10 | | | | | 15 | | |

| Leu | Glu | Glu | Glu | Ala | Pro | Gly | Ala | Ser | Leu | Trp | Pro | Thr | Thr | Val | Thr | Phe |
|---|---|---|---|---|---|---|---|---|---|---|---|---|---|---|---|---|
| | | 20 | | | | | 25 | | | | | 30 | | | | |

| Leu | Thr | Leu | Phe | Leu | Ile | Ser | Leu | Phe | Tyr | Ser | Thr | Ala | Leu | Thr | Val | Thr |
|---|---|---|---|---|---|---|---|---|---|---|---|---|---|---|---|---|
| 35 | | | | | 40 | | | | | 45 | | | | | 50 | |

| Thr | Val | Arg | Gly | Pro | Phe | Gly | Ser | Lys | Glu | Val | Pro | Gln | Tyr |
|---|---|---|---|---|---|---|---|---|---|---|---|---|---|
| | | | 55 | | | | | 60 | | | | | 65 |